United States Patent [19]

Thacker

[11] B 3,982,838

[45] Sept. 28, 1976

[54] COMPACT FAST ANALYZER OF ROTARY CUVETTE TYPE

[75] Inventor: Louis H. Thacker, Knoxville, Tenn.

[73] Assignee: The United States of America as represented by the United States Energy Research and Development Administration, Washington, D.C.

[22] Filed: Mar. 12, 1974

[21] Appl. No.: 450,521

[44] Published under the second Trial Voluntary Protest Program on February 17, 1976 as document No. B 450,521.

[52] U.S. Cl. ............................. 356/201; 250/564; 356/180; 356/225
[51] Int. Cl.[2] ........................................ G01N 21/24
[58] Field of Search ............ 356/39, 201, 204, 224, 356/225, 246, 180; 250/564, 565

[56] References Cited
UNITED STATES PATENTS

| | | | |
|---|---|---|---|
| 3,555,284 | 1/1971 | Anderson | 250/565 |
| 3,700,335 | 10/1972 | Seelbinder | 356/201 |
| 3,763,374 | 10/1973 | Tiffany et al. | 356/246 |
| 3,800,161 | 3/1974 | Scott et al. | 250/564 |
| 3,824,402 | 7/1974 | Mullaney et al. | 250/565 |

Primary Examiner—Alfred E. Smith
Assistant Examiner—Richard A. Rosenberger
Attorney, Agent, or Firm—Dean E. Carlson; D. S. Zachry; Stephen D. Hamel

[57] ABSTRACT

A compact fast analyzer of the rotary cuvette type is provided for simultaneously determining concentrations in a multiplicity of discrete samples using either absorbance or fluorescence measurement techniques. A rigid, generally rectangular frame defines optical passageways for the absorbance and fluorescence measurement systems. The frame also serves as a mounting structure for various optical components as well as for the cuvette rotor mount and drive system. A single light source and photodetector are used in making both absorbance and fluorescence measurements. Rotor removal and insertion are facilitated by a swing-out drive motor and rotor mount.

5 Claims, 1 Drawing Figure

U.S. Patent   Sept. 28, 1976   3,982,838
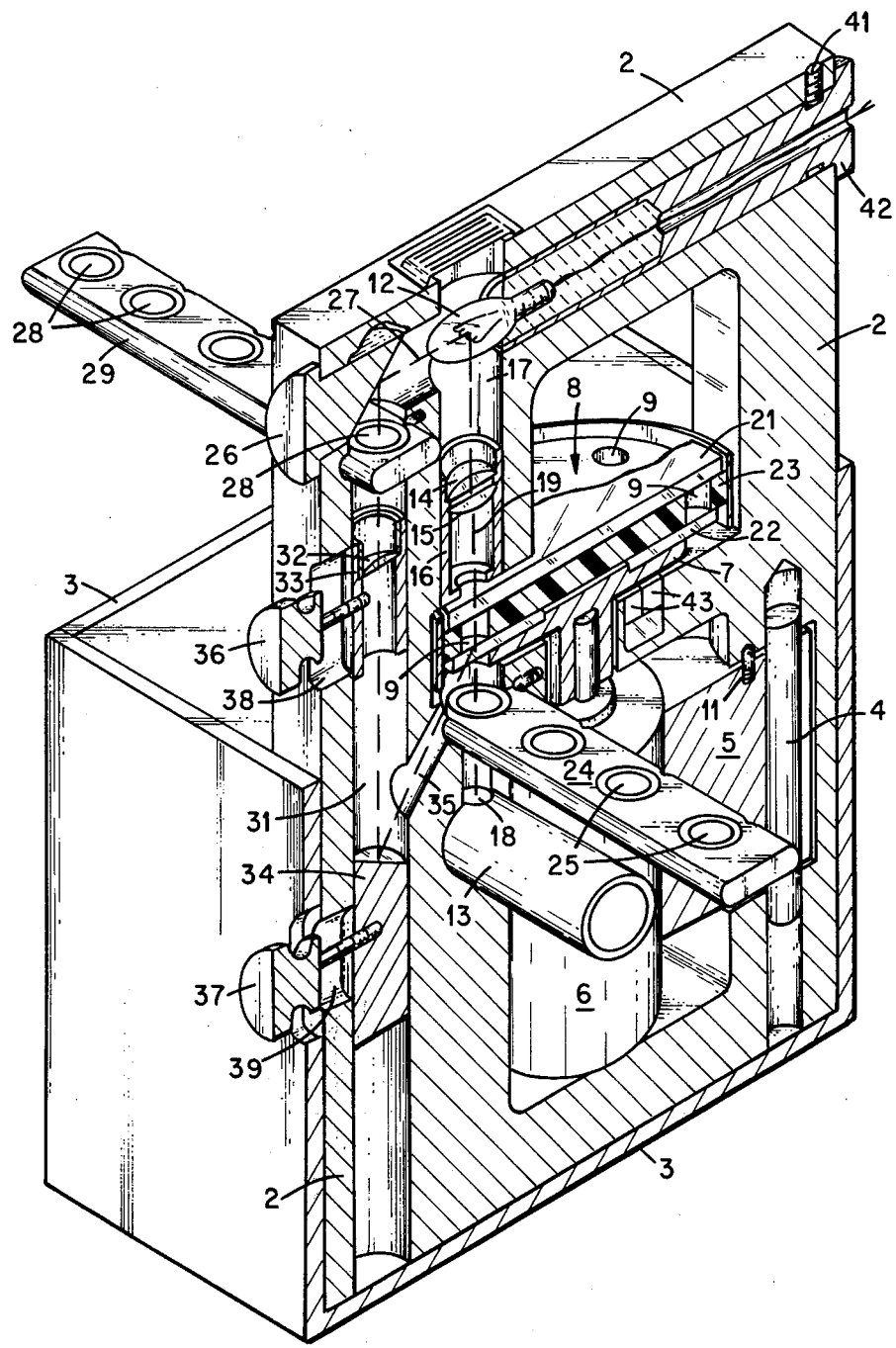

COMPACT FAST ANALYZER OF ROTARY CUVETTE TYPE

BACKGROUND OF THE INVENTION

The invention relates generally to concentration measuring instruments and more specifically to a compact fast analyzer of the rotary cuvette type which is suitable for making either absorbance or fluorescence measurements. It was made in the course of, or under, a contract with the U.S. Atomic Energy Commission.

A representative fast analyzer of the rotary cuvette type is described in U.S. Pat. No. 3,555,284 issued to common assignee on Jan. 12, 1971. In the fast analyzer described in that patent, acceleration forces associated with rotation are used to transfer and mix samples and reagents in a multi-cuvette rotor. Absorbance measurements are made by means of a stationary light source and photometer which scans the cuvettes during rotation. The signals thus generated are evaluated by a computer, allowing the reactions taking place in the respective cuvettes to be observed as they occur. Since all reactions are initiated simultaneously and are coupled with the continuous referencing of the spectrophotometric system of the analyzer, errors due to electronic, mechanical, or chemical drift are minimized.

A fast analyzer of compact design suitable for making either absorbance or fluorescence measurements is described in copending U.S. Pat. No. 3,800,161 issued Mar. 26, 1974, in the names of Charles D. Scott and Eddie T. Collins. According to that design, a multi-position pivoted optical head assembly supports means for directing light into sample holding cuvettes as they rotate. Means, selectively operable during a fluorometric measurement, for transmitting fluorescence emitted by samples within the cuvettes to a photodetector is also supported and selectively positioned by the optical head assembly. Rotor removal and insertion are accomplished by swinging the pivoted head assembly away from its operating positions to provide the necessary clearance.

It is a general object of the invention to provide an improved compact fast analyzer suitable for making absorbance or fluorescence measurements wherein the optical system is permanently aligned.

Another object of the invention is to provide an improved compact fast analyzer suitable for making absorbance or fluorescence measurements wherein changeover between the two types of measurement are made easily and with absolute repeatability.

Still another object of the invention is to provide an improved compact fast analyzer suitable for making absorbance or fluorescence measurements wherein rotors defining a rotary cuvette system may be inserted and removed without disturbing the analyzer's optical systems.

Other objects of the invention will be apparent to those versed in the art upon examination of the following written description of the invention and the appended drawings.

SUMMARY OF THE INVENTION

In accordance with the invention, a compact fast analyzer is provided for simultaneously determining concentrations in a multiplicity of discrete samples using either absorbance or fluorescence measurement techniques and rotors defining rotary cuvette systems. A rigid, generally rectangular frame defines optical passageways for absorbance and fluorescence measurement systems. The frame serves as a mounting structure for optical components within the measurement systems and for the rotor mount and drive system. A single light source and photodetector are used in making both absorbance and fluorescence measurements. Rotor insertion and removal are facilitated by a swing-out drive motor and rotor mount. The rigid frame structure maintains the optical system in permanent alignment despite rotor changes and changes in measurement mode, thereby ensuring accurate measurements.

DESCRIPTION OF THE PREFERRED EMBODIMENTS

The drawing is a sectioned isometric view of a fast analyzer made in accordance with the invention. As shown, an upstanding, generally rectangular frame 2 is mounted upright within a box-like housing 3. Pivotally attached to one side of frame 2 by means of a hinge pin 4 and bracket 5 are a swing-out drive rotor 6 and a rotor mount 7 which is driven by the motor. A removable rotor 8 defining a circular array of sample analysis cuvettes 9 is nested within the rotor mount which is shown swung into its normal operating or measuring position. Rotor mount 7 is provided with a circular array of perforations in its base corresponding to and in register with respective sample analysis cuvettes in rotor 8 so as to permit light passage through the cuvettes. Frame member 2 is suitably notched for receiving the rotor holder and rotor for reasons which will become apparent upon continued reading of the specification. A spring-loaded mechanical detent 11 engages bracket 5 to hold the motor and rotor holder in operating position. Alternatively, a conventional magnetic latch can be used to supplement or replace detent 11.

Separate optical paths are defined within frame 2 for making absorbance and fluorescence measurements. A single quartz-halogen lamp light source 12 and photomultiplier tube light detector 13 are used in common for both types of measurements, however.

Considering first the optical system associated with absorbance measurements, quartz focusing lenses 14 and 15 and lens holder 16 are situated immediately below lamp 12 within vertically extending passageway 17. Passageway 17 extends in axial alignment between lamp 12 and a light admission aperture 18 in the photomultiplier tube shield. Broken line 19 extending between lamp 12 and aperture 18 simulates the light path used in absorbance measurements.

Focusing lenses 14 and 15 provide intense illumination of samples contained in cuvettes 9 as they rotate through the light beam. Lens holder 16 is vertically adjustable by means of a slot and knob arrangement (not shown) similar to that described in later reference to the fluorescence optical system. As shown, rotor 8 is of a laminated or sandwich-type construction with transparent cover plates 21 and 22 closing the cuvettes formed within a central opaque disk 23. An absorbance filter holder 24, containing a plurality of different interference filters 25, is slidably fitted within a matching channel extending through frame 2 at a right angle to the axis of passageway 17. Filter holder 24 is positioned with the aid of a spring loaded mechanical detent and V-shaped notches in the side of the holder so as to place an interference filter 25 of desired wave length within the optical path intermediate the rotor 8 and photodetector 13.

Turning now to the optical system associated with fluorescence measurements, light from lamp 12 is reflected 90° by a front surface mirror 26 as indicated by broken line 27. The reflected light beam passes through one of a plurality of interference filters 28 mounted in a filter holder 29 slidably fitted within a matching channel extending through frame 2 at a right angle to the axis of passageway 31. A mechanical detent engages V-shaped notches in the side of holder 29 to ensure positive and accurate positioning of a selected filter within passageway 31. An opaque blank is provided in one of the filter openings to prevent light passage through passageway 31 when the analyzer is operating in the absorbance mode.

After passing through the interference filter, the light beam is focused by means of focusing lens 32 mounted within an adjustable lens holder 33 and then reflected 135° by a second front surface mirror 34 through passageway 35 to the bottom ends of cuvettes 9. The fluorescence emission from the sample in each cuvette passes downward through a suitable emission filter in holder 24 to light detector 13. A special rotor design is used which is similar to that used in absorbance measurements as described above but which has an opaque rather than transparent top cover plate 21 to prevent light passage through the cuvettes via the absorbance optics system.

Several adjustments may be made to components of the fluorescence optical system to obtain optimum positioning and to focus the fluorescence activation light beam where it intersects with the cuvettes. Mirror 26 may be rotated about its axis and/or displaced axially with respect to lamp 12 to achieve any desired lateral displacement of the light beam. Lens holder 33 and mirror 34 are also axially adjustable within passageway 31. As shown, lens holder 33 and mirror 34 are threadably engaged by adjustment knobs 36 and 37 which extend through elongated slots 38 and 39, respectively. With the adjustment knobs loose, the lens holder and mirror are moved to an axial position providing the desired light beam position and focus. The knobs are then tightened by turning until they are secured against frame 2 with the lens holder and mirror locked in position. A similar arrangement (not shown) is used to provide adjustment of lens holder 16. Focusing and positioning of the light beam may conveniently be accomplished by placing a ground glass plate or other translucent material within rotor mount 7 with the rotor mount at rest in its operating or measuring position and observing the light image projected thereon while adjusting the mirrors and focusing lens. Final fine adjustments to optimize light detector response may be made with a cuvette rotor containing fluorescent sample material in place.

Limited axial adjustment of lamp 12 may also be made to displace the light beam projected through the cuvettes during an absorbance measurement. A set screw 41 may be used to rigidly lock the lamp base 42 at any desired axial position within frame 2.

Light reflection transducers 43 containing photoemitting and photodetecting elements detect reflective marks on the bottom of the rotor mount 7 to provide cuvette synchronization signals for use in a data processing system (not shown). One commercially available transducer found suitable for use in the subject analyzer is the Model FPA transducer manufactured by Fairchild Microwave and Optoelectronics, a division of Fairchild Camera and Instrument Corporation. A power source and data processing system which may be used with the subject analyzer is described in copending application Ser. No. 411,553 of common assignee, filed Oct. 31, 1973, in the name of Wayne F. Johnson et al.

What is claimed is:

1. A compact fast analyzer of the rotary cuvette type suitable for selectively making both absorbance and fluorescence analyses of a multiplicity of samples comprising:
   a. an upstanding, rigid, rectangular frame defining first and second optical passageways;
   b. a light source disposed within said frame in optical communication with said first and second optical passageways;
   c. a photodetector disposed within said frame in optical communication with said first and second optical passageways;
   d. a motor-driven rotor mount pivotally attached to said frame, said rotor mount being selectively movable to an operating position intermediate said light source and photodetector and in optical communication with said first and second optical passageways and to a rotor loading position displaced from said operating position;
   e. a cuvette rotor defining a circular array of sample analysis cuvettes removably disposed on said rotor mount and rotatable therewith; and
   f. means for selectively blocking light passage through said first and second optical passageways.

2. The fast analyzer of claim 1 further including light focusing means disposed within said first and second optical passageways.

3. The fast analyzer of claim 1 further including means for selectively filtering light passing through said first and second optical passageways.

4. The fast analyzer of claim 3 wherein said means for selectively filtering light passing through said first and second optical passageways comprises elongated filter holders slidably fitted within said frame so as to pass through said passageways, a multiplicity of light filters being disposed within each of said filter holders so as to be selectively positionable within said passageways.

5. A compact fast analyzer of the rotary cuvette type suitable for selectively making both absorbance and fluorescence analyses of a multiplicity of samples comprising:
   a. a housing;
   b. an upstanding, rigid, rectangular frame partially enclosed within said housing, said frame defining first and second optical passageways and a slot intersecting said passageways for receiving a cuvette rotor;
   c. a light source disposed within said frame in optical communication with said first and second optical passageways;
   d. a photodetector disposed within said frame in optical communication with said first and second optical passageways;
   e. a motor driven rotor mount pivotally attached to said frame, said rotor mount being selectively movable to an operating position within said slot in optical communication with said first and second optical passageways and to a rotor loading position displaced from said operating position;
   f. a cuvette rotor defining a circular array of sample analysis cuvettes removably disposed on said rotor mount and rotatable therewith, rotation of said rotor in its operating position causing said cuvettes to sequentially and repeatedly be placed in optical communication with one of said optical passageways; and g. means for selectively blocking light passage through said first and second optical passageways.

* * * * *